United States Patent [19]

Curry-Hyde et al.

[11] Patent Number: 5,045,520

[45] Date of Patent: Sep. 3, 1991

[54] METHANOL SYNTHESIS CATALYST AND METHOD FOR THE PRODUCTION OF THE CATALYST

[75] Inventors: Henry E. Curry-Hyde; Mark S. Wainright; David J. Young, all of Sydney, Australia

[73] Assignee: Unisearch Limited, New South Wales, Australia

[21] Appl. No.: 459,712

[22] PCT Filed: Jun. 28, 1988

[86] PCT No.: PCT/AU88/00216

§ 371 Date: Jan. 22, 1990

§ 102(e) Date: Jan. 22, 1990

[87] PCT Pub. No.: WO89/00082

PCT Pub. Date: Jan. 12, 1989

[30] Foreign Application Priority Data

Jun. 29, 1987 [AU] Australia ............................... PI2762

[51] Int. Cl.$^5$ .............................................. B01J 25/00
[52] U.S. Cl. .................................................... 502/301
[58] Field of Search ............... 502/301, 342, 343, 345, 502/346

[56] References Cited

U.S. PATENT DOCUMENTS

| | | | |
|---|---|---|---|
| 4,349,464 | 9/1982 | Wanwright et al. | 502/301 |
| 4,366,260 | 12/1982 | Wainwright et al. | 502/342 X |
| 4,436,833 | 3/1984 | Broecker et al. | 502/176 |
| 4,843,101 | 6/1989 | Klier et al. | 502/343 X |

FOREIGN PATENT DOCUMENTS

38288/85 10/1987 Australia .

1081491 8/1967 United Kingdom .

OTHER PUBLICATIONS

Curry-Hyde et al "Preparation and Properties ... " Applied Catalysis 29 (1987) pp. 31-41.
Tomsett et al. "Structural Changes ... " Applied Catalysis 33(1987) 119-127.
Warwick et al "Zinc-Promoted Raney ... " Prod. Res. & Dev. vol. 19 p. 551 12/1980.
Friedrich et al "Methanol Synthesis ... " Jour. of Catalysis 80(1983) 1-13.
Friedrich et al "Methanol Synthesis ... " Jour. of Catalyst 80(1983) 14-24.
Bridgewater et al "Methanol Synthesis over ... " Applied Catalysis 7 (1983) pp. 369-382.
Bridgewater et al "A Comparison of Raney ... " Applied Catalysis 28(1986) pp. 241-253.
Abstract #127494c "Catalyst and Method ... " Catalysis, Kinetics vol. 100 1984, p. 405.

*Primary Examiner*—W. J. Shine
*Attorney, Agent, or Firm*—Nixon & Vanderhye

[57] ABSTRACT

Method for the production of a catalyst suitable for use in the synthesis of methanol obtained by reacting carbon monoxide, carbon dioxide or mixtures thereof, with hydrogen, comprising forming an alloy containing 0 to 50 weight percent zinc, 30 to 75 weight percent aluminum and the balance being substantially all copper, and extracting aluminum from the alloy using an effective concentration of zincate ions in an aqueous solution of an alkali metal hydroxide. Catalysts made by this method are disclosed, together with their use in the preparation of methanol.

11 Claims, No Drawings

METHANOL SYNTHESIS CATALYST AND METHOD FOR THE PRODUCTION OF THE CATALYST

FIELD OF THE INVENTION

The present invention relates to a process for the production of catalysts, useful in the synthesis of methanol, to the catalysts so produced and to a process for the production of methanol using such catalysts.

BACKGROUND ART

Marsden et al. Industrial & Engineering Chemistry Product Research and Development, 19 551 (1980) were the first to show that an active low temperature methanol synthesis catalyst can be produced by leaching small particles of a Cu-Al-Zn alloy in sodium hydroxide solutions. In other studies, Friedrich et al. J. Catal. 80 1, 14 (1983) and Bridgewater et al. Appl. Catal. 7 369 (1983) using small particles, have investigated the effect of alloy composition on catalyst activity. This technique of catalyst preparation has been fully described in U.S. Pat. No. 4,349,464 and U.S. Pat. No. 4,366,260.

A recent study, Curry-Hyde et al. Appl. Catal. 29 31 (1987) has been concerned with the preparation of catalysts by the method described in the patents. In this study, an alloy of optimal composition was used to study preparation and characteristics of the Raney catalyst in pellet form. It was found that the long times required to leach the large particles had two detrimental effects on the nature of the catalyst. The first decreased the overall pellet surface area after long periods of leaching, whilst the second caused a decrease in the specific activity of the catalyst.

The decrease in pellet surface area was as a result of the physical rearrangement of copper crystallites in the porous copper whilst the alloy core was still being leached. The decreased activity resulted from decreases in zinc oxide concentrations on the copper surface. These were caused by secondary leaching effects on the zinc oxide that become significant at long leach times.

Previous investigations sought to improve the zinc oxide content in the leached Cu structures by changing the ZN content of the Al-Cu-Zn alloy, as described in Friedrich et al. J. Catal. 80 1, 14 (1983) and Bridgewater et al. Appl. Catal. 7 369 (1983).

DISCLOSURE OF INVENTION

Surprisingly, the present inventors have discovered an improved method for producing zinc oxide promoted Raney copper catalysts using a leaching/precipitation technique to give higher concentrations and improved distributions of zinc oxide in the catalytic material.

Accordingly, the present invention consists in a method for the production of a low temperature methanol synthesis catalysts composition suitable to synthesize methanol by the reaction of carbon monoxide or carbon dioxide of mixtures thereof with hydrogen, comprising forming an alloy containing 0 to 50 wt. % zinc, 30 to 75 wt. % aluminum, the balance being substantially all copper and extracting aluminum from the alloy using an effective concentration of zincate ions in an aqueous solution of an alkali metal hydroxide.

In a further aspect the present invention consists in a methanol synthesis catalyst produced by the foregoing method.

In a still further aspect the present invention consists in a process for the production of methanol comprising contacting a gaseous mixture of carbon monoxide or carbon dioxied, or mixtures thereof, and hydrogen with a catalyst according to the present invention.

It is believed that the extraction of the alloy in sodium zincate-sodium hydroxide solutions results in catalytic material with higher concentrations and improved distributions of ZnO after extracting, than the method described in U.S. Pat. No. 4,349,464 and U.S. Pat. No. 4,366,260 of extracting Raney alloys in sodium hydroxide solutions. The catalytic material prepared according to the present invention has both higher surface area and higher material activities than the catalytic material prepared by the previous invention.

The alloy from which the catalysts according to present invention are formed preferably comprises 0 to 20 wt. % zinc, 40 to 50 wt. % aluminum and 40 to 50 wt. % copper. Most preferably the alloy comprises 17 wt. % zinc, 39 wt. % aluminum and 44 wt. % copper.

Generally, the alloy will be formed as particles, which depending on the final use, may vary over a wide size range.

The zincate ions are suitably in a concentration of from 0.01 to 1 molar, more preferably in a concentration of from 0.4 to 1 molar. The alkali metal hydroxide used to extract the alloy is preferably sodium hydroxide and the source of zincate ions is sodium zincate. The sodium zincate concentration in the sodium hydroxide solution may be between 0.01 and 1M $Na_2An(OH)_4$, preferably between 0.4 and 1M.

The aqueous sodium hydroxide concentration may be between 0.1 and 12M NaOH, preferably 2 and 8M. The extraction may be carried out at temperatures between 274 and 374K, preferably between 274K and 303K.

MODES FOR CARRYING OUT THE INVENTION

Catalyst Preparation

In this example, Raney copper zinc catalysts are produced from two alloys molded in the form of pellets. To show the range of application of the preparation technique, one alloy was zinc free and the other contained zinc. It will be appreciated that other combinations of Cu, Al and Zn could be used and that geometries other than the pellet form used for this example, could be used.

Pellets of $CuAl_2$ alloy (53 wt. % Cu, 47 wt. % Al) and Cu-Al-Zn alloy (43.2 wt. % Cu, 39 wt. % Al, 17.8 wt. % Zn), (3.8 mm×5.4 mm dia), were leached in large excesses of two different leach solutions, 6.1M sodium hydroxide and 0.62M zincate in 6.1M sodium hydroxide. Leaching was terminated by washing the pellets in distilled water to a pH of 7. To simplify references to the four Raney catalysts Table 1 identifies them according to the precursor alloys and leach conditions used.

TABLE 1

A summary of alloys and leach solutions used to prepare the Raney catalysts. The labels reference each catalyst in the text.

| Alloy | Leach Solution | Temp (K) | Catalyst | Label |
|---|---|---|---|---|
| CuAl₂ | 6.1 M NaOH | 274 | Raney Cu | RC |
| CuAl₂ | 0.62 M Na-zincate/NaOH | 274 | Raney Cu—(Zn doped) | RCD1 |
| CuAl₂ | 0.62 M Na-zincate/NaOH | 303 | Raney Cu—(Zn doped) | RCD2 |
| Cu—Al—Zn | 6.1 M NaOH | 303 | Raney Cu—Zn | RCZ |
| Cu—Al—Zn | 0.62 M Na-zincate/NaOH | 303 | Raney Cu—Zn(Zn doped) | RCZD |

TABLE 2

Physical properties of the Raney copper catalyst produced by leaching Raney alloys in sodium zincate sodium hydroxide solutions and sodium hydroxide solutions.

| Catalyst label | Leach time (h) | Leach depth (mm) | Surface area pellet ($m^2$) | Surface area material ($m^2/cm^3$) | Cu | Zn (wt %) | Al |
|---|---|---|---|---|---|---|---|
| CuAl₂* | | | | | | | |
| RC | 135 | 0.77 | 4.0 | 66 | 98.2 | 0.0 | 1.8 |
| RCD | 522 | 0.81 | 10.9 | 174 | 86.3 | 7.8 | 5.9 |
| Cu—Al—Zn* | | | | | | | |
| RCZ | 48 | 0.81 | 5.1 | 72 | 93.5 | 3.6 | 2.8 |
| RCZD | 111 | 0.87 | 6.7 | 102 | 91.7 | 6.2 | 2.1 |

*Alloys used to prepare catalyst by extraction. The labels refer to the catalysts prepared under the conditions described in Table 1.

After washing, 5 cm³ of moist Raney catalyst pellets and 5 cm³ of unleached inactive alloy pellets (as diluent) were loaded into a reactor 38 mm internal diameter and 150 mm long. The catalyst was dried for 1 hour at 90° C. in a flow of 100% H₂ by immersing the reactor in an oil bath, and the temperature was raised to 160° C. for a further hour. The reactor was then transferred to a molten salt bath at 220° C. under pure H₂ for approximately 1 hour and the catalyst was then ready for activity testing as no further water was produced during the latter part or this period.

Activities of all catalysts for methanol synthesis was measured at 220° C. and 4500 kPa. The syngas mixture was contained 5±0.2% $CO_2$ and 4±0.2% $CO_2$ in $H_2$ was used at a GHSV (NTP) of 36,000 h⁻¹. These conditions closely represent industrial practice.

Results and Discussion

The physical properties of the catalysts used for this example are present in Table 2. The two catalysts produced from CuAl₂ show the effect of leaching a zinc free alloy in sodium hydroxide (catalyst RCD). The alloy pellets were leached to approximately the same depth. The leach depths representing only partial leaching of the pellets. The leaching time required to extract the alloy pellet to the reported leach depth in zincate-rich solution (catalyst RCD) was considerably slower than in the sodium hydroxide solution. The pellet surface area of the RCD catalyst pellet, partially leached in he zincate ion containing solution, was higher, than was found for the RC catalyst pellets produced by leaching in sodium hydroxide. The surface area of the leached material on its own was significantly higher than of the RC catalyst. The composition analysis of the leached material showed that leaching the CuAl₂ alloy pellets in the zincate ion containing solutions produced the RCD catalyst containing Zn as well as the components found in the RC catalyst, Cu and Al. The Al content in the RCD catalyst was found to be higher than in the RC catalyst.

Table 2 also reports examples of catalyst RCZ and RCZD produced from an alloy containing Zn. These were prepared by leaching in sodium hydroxide according to the method disclosed in U.S. Pat. No. 43,949,464 and leaching in sodium zincate containing sodium hydroxide solution according to this invention, respectively. The leaching conditions were reported in Table 1.

The RCZD catalyst took longer to be leached to a leach depth similar to the RCZ catalyst. The surface area of the RCZD catalytic material was found to be higher than for the RCZ catalyst. The Zn content of the RCZD catalytic material was also significantly higher than the RCZ catalyst, and both materials had similar Al contents.

TABLE 3

Activity properties of Raney copper catalysts produced by leaching Raney alloys in sodium zincate containing sodium hydroxide solutions and in sodium hydroxide solutions.

| Catalyst label | Specific activity (mol/m²/h) × 10⁴ | Material activity (mol/cm$_{mat}^3$/h) × 10³ | Production Rate (Kg/l$_{cat}$/h) |
|---|---|---|---|
| CuAl₂ | | | |
| RC | 0.47 | 3.3 | 0.048 |
| RCD | 2.46 | 39.7 | 0.57 |
| Cu—Al—Zn | | | |
| RCZ | 4.37 | 29.4 | 0.36 |
| RCZD | 6.39 | 62.7 | 0.98 |

Table 3 shows the specific activity (obtained by dividing activity per unit mass by the BET surface area) for the catalysts reported in Table 2. The specific activity of catalyst RCD was approximately 5 times higher than catalyst RC. This was attributed to the presence of Zn in the leached material deposited from the zincate containing solution during leaching.

Studies have shown that the continuous copper surface of Raney Copper is only mildly active and that zinc deposits on the surface promote hydrogenation of carbon oxides through secondary interaction with the adsorbed species. The material surface area of catalyst RCD (Table 2) was also higher than that found for the RC catalyst. The improved surface area of the leached material and the higher specific activity of the RCD catalyst results in a material activity of the RCD catalyst being approximately 10 times greater than that found for the RC catalyst.

A comparison of activity characteristics between the RCZ catalyst prepared according to U.S. Pat. No. 4,349,464 and U.S. Pat. No. 4,366,260 and the RCZD catalyst prepared according to this invention is reported in Table 3. It shows that the RCZD catalyst has an improved specific activity. This has been attributed to the higher Zn content and relatively unchanged Al content of the catalytic material reported in Table 2. The RCZD catalyst also has higher surface area than the RCZ catalyst, consequently, the material activity of the RCZD catalyst is significantly higher than that of the RCZ catalyst.

Table 4 summarizes the best methanol yields achieved using the different techniques for preparing the Raney Cu-ZnO-Al$_2$O$_3$ catalysts. These comparisons show that the invention described in this specification results in a Raney Cu-ZnO-Al$_2$O$_3$ catalyst (RCZD, RCD1, RCD2) which is superior to the Raney copper zinc methanol synthesis catalysts (RCZ) prepared according to U.S. Pat. No. 4,349,464 and U.S. Pat. No. 4,366,260.

TABLE 4

Highest yields for Raney catalysts (produced at different leaching conditions) compared to coprecipitated catalysts tested under the same conditions and other catalysts reported in the literature.

| Catalyst (kg/l$_{cat}$/h) | *Preparation | Temperature | Pressure (atm) | Space velocity | Yield |
| --- | --- | --- | --- | --- | --- |
| RCZD | I | 220 | 45 | 36000 | 1.12 |
| RCZD | I | 220 | 45 | 15000 | 0.80 |
| RCD1 | IIa | 220 | 45 | 36000 | 0.64 |
| RCD2 | IIb | 220 | 45 | 36000 | 0.61 |

TABLE 4-continued

Highest yields for Raney catalysts (produced at different leaching conditions) compared to coprecipitated catalysts tested under the same conditions and other catalysts reported in the literature.

| Catalyst (kg/l$_{cat}$/h) | *Preparation | Temperature | Pressure (atm) | Space velocity | Yield |
| --- | --- | --- | --- | --- | --- |
| RCZ | III | 220 | 45 | 12000 | 0.60 |

*Preparation
I Cu—Al—Zn leached in 6.1 M NaOH/0.62 M Na-zincate, at 303K;
II Cu—Al$_2$ leached in 6.1 M NaOH/0.62 M Na-zincate, (a) 274K (b) 303K;
III Cu—Al—Zn leaching 6.1 M NaOH, at 274K

We claim:

1. A method for the production of a low temperature methanol synthesis catalyst composition suitable to synthesize methanol by the reaction of carbon monoxide or carbon dioxide or mixtures thereof, with hydrogen, comprising forming an alloy containing 0 to 50 wt % zinc, 30 to 75 wt % aluminum, the balance being substantially all copper and extracting aluminum from the alloy using an effective concentration of zincate ions in an aqueous solution of an alkali metal hydroxide.

2. A method as in claim 1 wherein the alloy is in the form of pellets.

3. A method as in claim 1 wherein the alloy comprises 0 to 20 wt. % zinc, 40 to 50 wt % aluminum and 40 to 50 wt. % copper.

4. A method as in claim 3 wherein the alloy comprises 17 wt % zinc, 39wt % aluminum and 44 wt % copper.

5. A method as in claim 1 wherein the zincate ions are in a concentration of from 0.01 to 1 molar.

6. A method as in claim 5 wherein the zincate ions are in a concentration of from 0.4 to 1 molar.

7. A method as in claim 1 wherein the alkali metal hydroxide is sodium hydroxide in a concentration of from 0.1 to 12 molar.

8. A method as in claim 7 wherein the sodium hydroxide is in a concentration of from 2 to 8 molar.

9. A method as in claim 1 wherein the alloy is extracted at a temperature of between 274 and 374K.

10. A method as in claim 9 wherein the temperature of extraction is between 274K and 303K.

11. A low temperature methanol synthesis catalyst suitable to synthesize methanol by the reaction of carbon dioxide or carbon monoxide or mixtures thereof with hydrogen, prepared by a method according to claim 1.

* * * * *